US010345262B1

(12) United States Patent
Kalafut et al.

(10) Patent No.: US 10,345,262 B1
(45) Date of Patent: Jul. 9, 2019

(54) METHOD AND APPARATUS FOR ANALYZING A SAMPLE BY HIGH-FIELD ASYMMETRIC WAVEFORM ION MOBILITY-MASS SPECTROMETRY

(71) Applicant: Thermo Finnigan LLC, San Jose, CA (US)

(72) Inventors: Bennett S. Kalafut, San Jose, CA (US); Rae Ana Snyder, San Jose, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 31 days.

(21) Appl. No.: 15/844,291

(22) Filed: Dec. 15, 2017

(51) Int. Cl.
*G01N 27/64* (2006.01)
*G01N 27/62* (2006.01)
*G01N 33/68* (2006.01)
*G01N 30/72* (2006.01)
*H01J 49/00* (2006.01)

(52) U.S. Cl.
CPC ....... *G01N 27/624* (2013.01); *G01N 30/7233* (2013.01); *G01N 33/6848* (2013.01); *H01J 49/0031* (2013.01)

(58) Field of Classification Search
USPC ........................................................ 250/283
See application file for complete search history.

(56) References Cited

U.S. PATENT DOCUMENTS

| 6,639,212 B1 | 10/2003 | Guevremont et al. |
| 7,045,776 B2 * | 5/2006 | Kaufman ............. G01N 27/624 250/281 |
| 7,800,055 B2 * | 9/2010 | Geromanos ........ G01N 30/7233 250/288 |
| 8,927,925 B2 * | 1/2015 | Kuehl ................. H01J 49/0036 250/282 |

OTHER PUBLICATIONS

D'Addario; et. al, "A modular computational framework for automated peak extraction from ion mobility spectra", BMC Bioinformatics, 2014, pp. 15-25 (Year: 2014).*

* cited by examiner

*Primary Examiner* — Phillip A Johnston
(74) *Attorney, Agent, or Firm* — A. J. Gokcek

(57) ABSTRACT

A method of analyzing a sample by high-field asymmetric waveform ion mobility-mass spectrometry (FAIMS-MS) is disclosed. An ion beam containing ions of a plurality N of isomers is directed into a FAIMS device. The compensation voltage (CV) at which the FAIMS device is operated is varied among a plurality M of values. For each of the M CV values, an intensity of the ion beam transmitted by the FAIMS device, or product ions derived therefrom, is measured at a mass-to charge ratio corresponding to the plurality N of isomers. The intensities of each of the plurality N of isomers is determined using a set of linear equations, relating the weighted measured intensity values at each value M of the CV and the intensities of each of the N isomers when the FAIMS device is in a non-separation condition.

18 Claims, 6 Drawing Sheets

METHOD AND APPARATUS FOR ANALYZING A SAMPLE BY HIGH-FIELD ASYMMETRIC WAVEFORM ION MOBILITY-MASS SPECTROMETRY

FIELD OF THE INVENTION

This invention relates generally to high field asymmetric ion mobility spectrometry (FAIMS), and more particularly to methods and apparatuses for quantifying mixed isomers using FAIMS.

BACKGROUND OF THE INVENTION

In ion mobility spectrometry devices, separation of gas-phase ions is accomplished by exploiting variations in ion drift velocities under an applied electric field arising from differences in ion mobility. One well-known type of ion mobility spectrometry device is the High Field Asymmetric Waveform Ion Mobility Spectrometry (FAIMS) cell, also known by the term Differential Ion Mobility Spectrometry (DMS) cell, which separates ions on the basis of a difference in the mobility of an ion at high field strength relative to the mobility of the ion at low field strength. Briefly described, a FAIMS cell comprises a pair of electrodes (e.g., planar electrodes or cylindrical electrodes) separated by a space that defines an ion separation region through which ions are passed. During transit, ions in the separation gap experience an alternating electric field. The alternating field, which can be a bi-sinusoidal RF waveform, has high field portions and low field portions that are asymmetric but of equal area and opposite sign. Ions can have different mobilities in the high and low portions of the cycle. The mobilities of some ions can, for example, be higher during the high period of the waveform compared to the low period of the waveform. Ions of such mobility behavior in FAIMS can deviate away from the inner RF applied electrode and annihilate on the outer electrode over multiple RF cycles of the waveform. However, a DC offset (compensation voltage, or CV) can be applied to the outer electrode to correct for the trajectory such that the ion can be transmitted through the FAIMS device. Alternatively, a time-varying set of ions can be transmitted by sweeping the CV and generating a FAIMS spectrum of ion current versus CV.

FAIMS devices may be used for a variety of purposes. As an MS-compatible separation technique, FAIMS is useful in separating isomers which cannot be resolved by MS or MS/MS alone as isomers have the same mass but different structures. Design of FAIMS devices can involve trading off separation for transmission efficiency or shorter ion transit time, and the high-field and low-field mobilities of isomers often differ from each other, resulting in isomer-specific CV tunings.

While the optimal CV tunings for transmission of different ion species may differ, their CV tuning curves—the relationship between the transmitted flux and the CV for a given ion species—often overlap. This problem is exacerbated as the number of isomers (e.g., in a sample of mixed isomers) to be separated increases, since the likelihood that at least some of the CV tuning curves overlap grows with more isomers. This prevents the use of FAIMS as a mere filter of unwanted components in a mixture of isomers, complicating the use of FAIMS-MS (or FAIMS-MS/MS) for isomer quantification.

FIG. 1 is a simple example of tuning curves for three isomers, used here to highlight the problem presented by overlapping CV tuning curves. The two rightmost tuning curves overlap significantly with the leftmost tuning curve and even more significantly with each other. In an attempt to separate out a single isomer, a CV must be selected for which the other tuning curves exhibit transmission of nearly zero. Considering the isomer corresponding to the middle tuning curve, this is not possible at all. Considering the isomer corresponding to the leftmost tuning curve, at the optimal CV for transmission, the other two isomers are still transmitted at about 5% of the maximum possible intensity. This contribution can be added to the measurement uncertainty if their relative concentrations can be estimated. But if the other isomers are present in excess of the isomer of interest they can be the major contribution to the signal at the detector even at 5% of their peak intensities. Tuning the isomer of interest away from its optimum CV can sometimes remove more of the contributions of the other isomers to the signal, but even when this is possible it comes at the expense of sensitivity.

What is needed is a method of using FAIMS-MS and a corresponding apparatus for quantification of isomers in mixtures having overlapping CV tuning curves.

SUMMARY

Embodiments of the present invention disclose methods and apparatuses for analyzing a sample by FAIMS-MS. In one embodiment, the method includes directing an ion beam containing ions of a plurality N of isomers, where N is at least 2, into a FAIMS device and varying the compensation voltage (CV) at which the FAIMS device is operated among a plurality M of values where M≥N. For each of the M CV values, the intensity of the ion beam transmitted by the FAIMS device, or products ions derived therefrom, is measured at a mass-to-charge ratio corresponding to the plurality N of isomers. The method also includes determining the intensities of each of the plurality N of isomers using the relation: $w\varnothing=\Phi$, where w is an empirically derived weighting matrix, $\varnothing$ is a vector $\varnothing_1 \ldots \varnothing_N$ of the intensities of each of the plurality N of isomers without FAIMS (i.e., in non-separating mode), and $\Phi$ is a vector $\Phi_1 \ldots \Phi_M$ of the measured intensity values at each of the M values of the compensation voltage. The relation $w\varnothing=\Phi$ may be solved for $\varnothing$ using one of the following techniques: matrix inversion, ordinary least squares, weighted least squares, and a generalized linear model (GLM) algorithm.

The elements of the weighting matrix w may be set using CV tuning curves acquired for each of the N isomers in pure form, i.e., in the absence of the other isomers.

In some embodiments, the isomers comprise isomers of a peptide or protein.

In some embodiments, the step of measuring the intensity of the ion beam includes mass filtering the ion beam to only transmit ions of the m/z corresponding to the isomer and detecting the transmitted ions. In other embodiments, the step of measuring the intensity of the ion beam includes mass filtering the ion beam to only transmit ions of the m/z corresponding to the isomer, fragmenting the transmitted ions to generate product ions, mass filtering the product ions to only transmit ions corresponding to the isomer, and detecting the transmitted product ions.

In some embodiments, the M CV values include at least one of the following determined from the tuning curves: CV values that maximize the transmission of each isomer, CV values at crossings of the tuning curves along a boundary of a region enclosed by all of the tuning curves, and outermost CV values on the tuning curves mirroring a nearest crossing point.

In some embodiments, the ion beam is formed from a chromatographically separated sample, and the method further includes the step of integrating the determined intensity contribution of an isomer over a chromatographic peak.

The step of determining the intensity contribution of each of the plurality N of isomers may be performed in real time.

In another embodiment of the present invention, an apparatus is provided. The apparatus includes an ion source for generating a beam of ions from a sample. The apparatus also includes a FAIMS device positioned to receive the beam of ions from the ions source. The FAIMS device has a compensation voltage (CV) of variable magnitude applied to it. The apparatus also includes at least one mass filter positioned to receive ions from the FAIMS device and operable to selectively transmit ions of a specified mass-to-charge ratio, and a detector for generating a signal representative of a measured intensity of ions transmitted by the at least one mass filter. The apparatus further includes a data/control system programmed to perform the following steps: varying the CV at which the FAIMS device is operated among a plurality M of values; causing the at least one mass filter to transmit ions at an m/z corresponding to a plurality N of isomers contained in the sample; and determining the intensities of each of the plurality N of isomers using the relation: $w\emptyset = \Phi$, where w is an empirically derived weighting matrix, $\emptyset$ is a vector of the intensities of each of the plurality N of isomers without FAIMS (e.g., the FAIMS device turned off, the FAIMS device turned on but removed from the ion beam path, or the FAIMS device turned on but having a symmetrical waveform applied to it), and $\Phi$ is a vector of the measured intensity values at each of the M values of the compensation voltage.

DETAILED DESCRIPTION OF EMBODIMENTS

Figure 1:
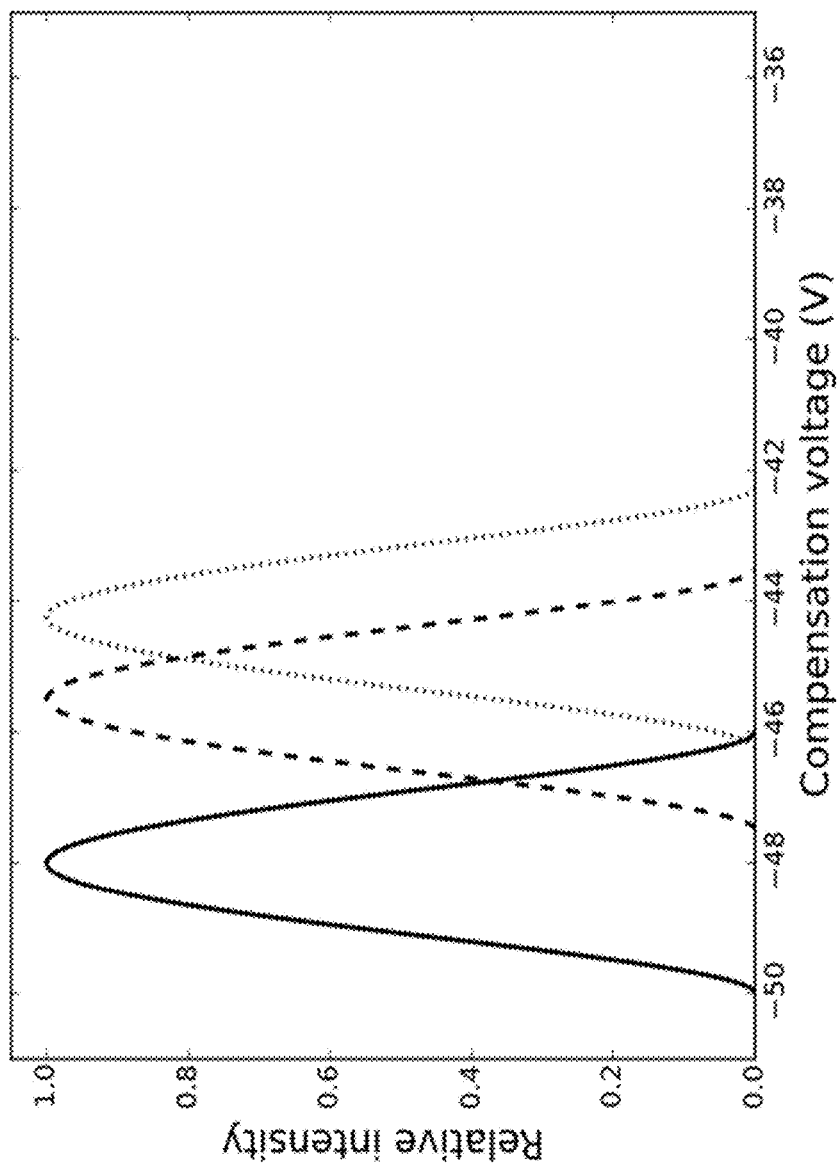
FIG. 1 is an example of a tuning curve for three isomers, used here to highlight the problem of overlapping CVs.
Figure 2A:
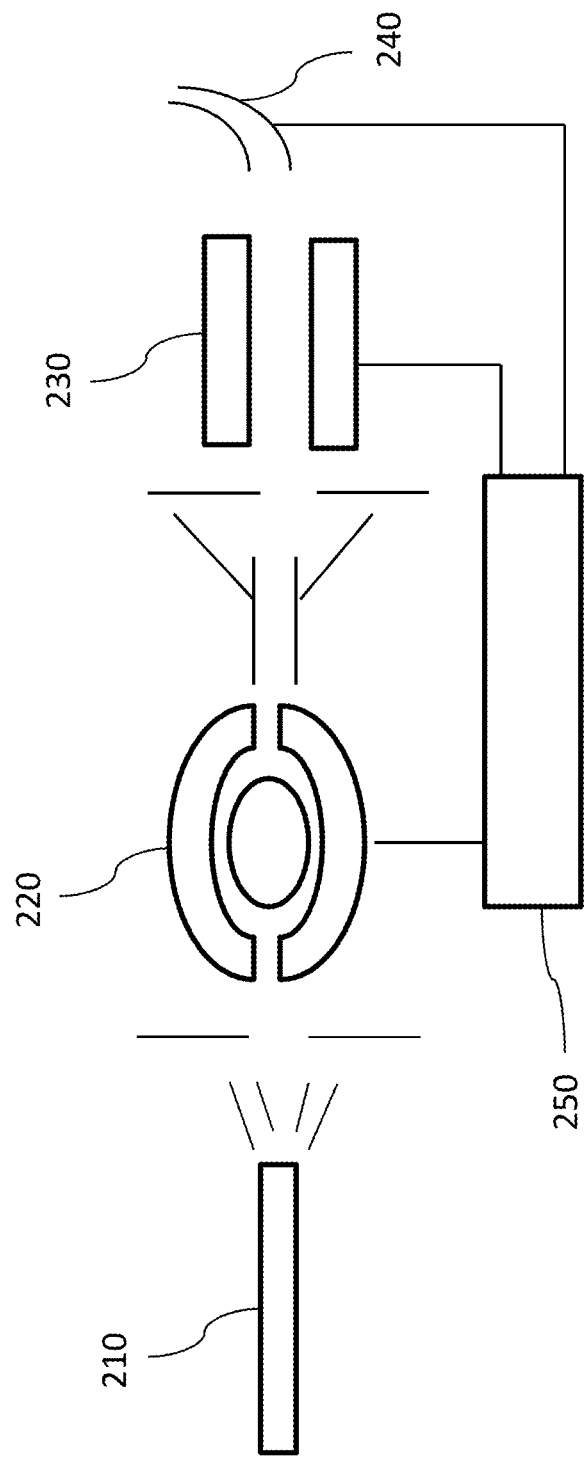
FIG. 2A is a simplified schematic diagram of an apparatus for analyzing a sample by high-field asymmetric ion mobility-mass spectrometry (FAIMS-MS), in accordance with one embodiment of the present invention.

FIG. 2A is a simplified schematic diagram of an apparatus for analyzing a sample by high-field asymmetric ion mobility-mass spectrometry (FAIMS-MS), in accordance with one embodiment of the present invention. A solution of sample to be analyzed is introduced as a spray of liquid droplets into an ionization chamber via atmospheric pressure ion source 210. The ion source 210 may be configured as an electrospray ionization (ESI) source, wherein a high DC voltage (either positive or negative) is applied to a capillary or "needle" through which the sample solution flows. Other suitable ionization techniques may be utilized in place of ESI, including without limitation such well-known techniques as atmospheric pressure chemical ionization (APCI), heated electrospray ionization (HESI), and thermospray ionization.

The ion source 210 generates a beam of ions which are passed to a FAIMS device 220 through an aperture. FAIMS device 220, which will be explained below with reference to FIG. 2B, causes the ions to become temporally separated according to their ion mobility. Those ions that are transmitted to the FAIMS device 220 are then transported to at least one mass filter 230. Mass filter 230 may be implemented as one or a combination of conventional mass filters, including (without limitation) a quadrupole mass analyzer. The mass filter 230 is configured to selectively transmit ions of a specified mass-to-charge (m/z) ratio. Detector 240 generates a signal representative of a measured intensity of ions transmitted by the at least one mass filter 230. The apparatus further includes a data/control system 250 programmed to vary the CV at which the FAIMS device 220 is operated among M pre-selected values, cause the at least one mass filter 230 to transmit ions at an m/z corresponding to a plurality of isomers contained in the sample, and to determine the intensities of each one of the plurality N of isomers at a non-separation (without FAIMS) condition in accordance with the method steps described below. It should be noted that the term "without FAIMS", as used herein, refers to the condition where the intensities of the isomers are obtained without differential mobility of the ions.

Figure 2B:
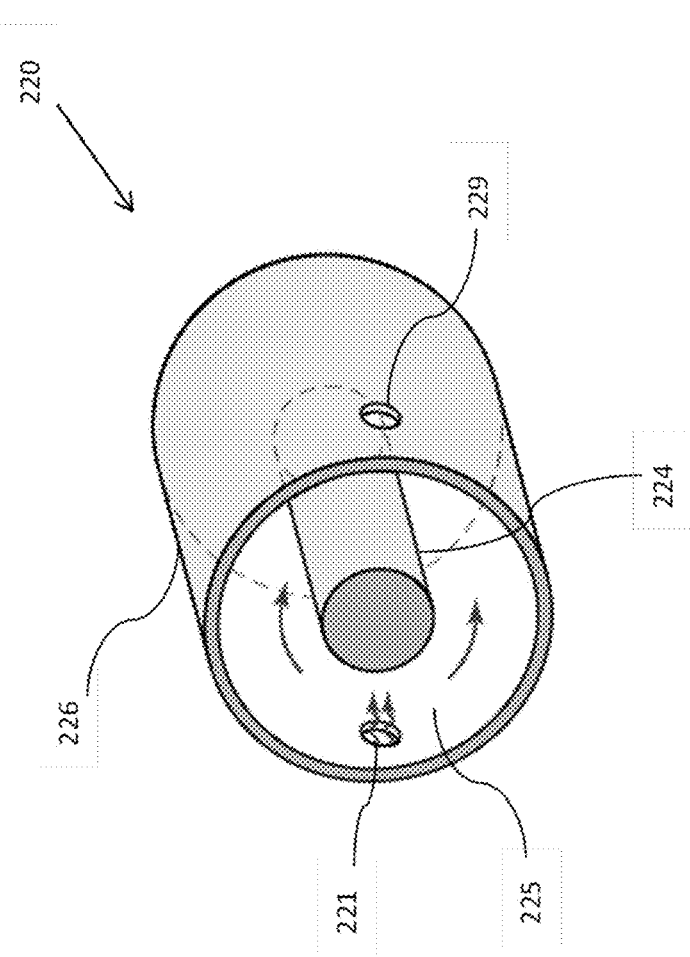
FIG. 2B is a prior art FAIMS device including inner and outer electrodes having radially opposed surfaces, which can be utilized in the apparatus of FIG. 2A.

Referring to FIG. 2B, the FAIMS device 220 includes inner and outer electrodes 224 and 226 having radially opposed surfaces, which define there between an annular separation region 225 (an "analytical gap") through which the isomers are transported. The FAIMS device geometry depicted in FIG. 2 may be generally referred to as a "side-to-side FAIMS cell", in which the longitudinal axes (axes of cylindrical surfaces, directed out of the page) of inner electrode 224 and outer electrode 226 are oriented transversely with respect to the overall direction of ion flow. The basic principles of the design and operation of FAIMS devices and other ion mobility spectrometry devices have been extensively described elsewhere in the art (see, for example, U.S. Pat. No. 6,639,212 to Guevremont et al.), and hence will not be described in detail herein. In brief, the carrier gas and isomers flow through the separation region 225 from inlet orifice 221 to exit orifice 229. Isomer separation is effected within the separation region (analytical gap) 225 of the FAIMS device 220 by applying an asymmetric waveform having a peak voltage (DV) and a compensation voltage (CV) to one of the inner or outer electrodes, 224, 226. The values of CV and DV are set to allow transmission of a selected isomer species through separation region 225. Other isomer species having different relative values of high field and low field mobilities will migrate to the surface of one of the electrodes and be neutralized. Methods of selecting the CV values to measure intensities of an ion beam transmitted through the FAIMS device will be described below and with reference to FIG. 3 hereinafter.

Figure 3:
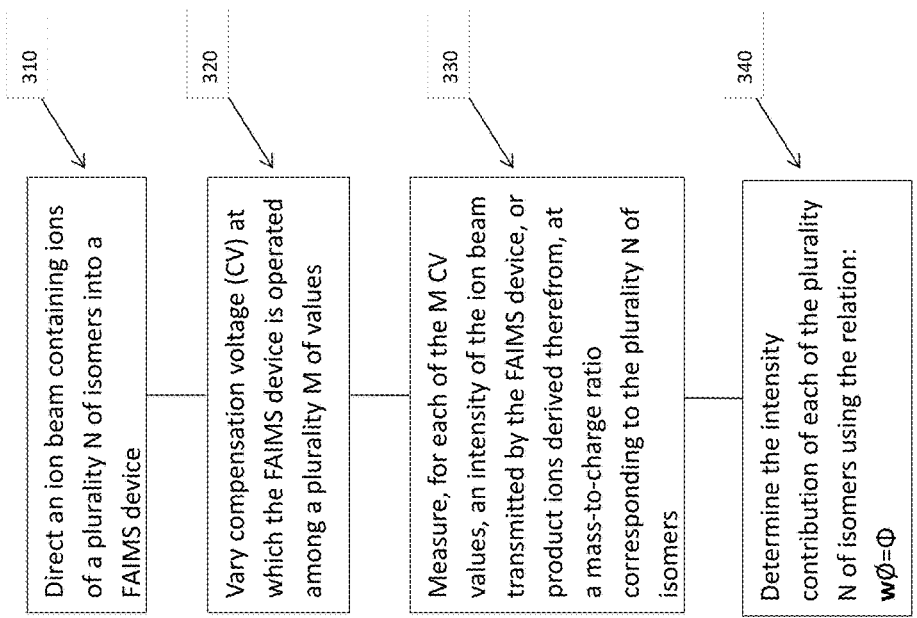
FIG. 3 is a flowchart depicting steps of a method of analyzing a sample by FAIMS-MS, in accordance with one embodiment of the present invention.

FIG. 3 is a flowchart depicting steps of a method of analyzing a sample by FAIMS-MS, in accordance with one embodiment of the present invention. In the initial step 310, an ion beam containing ions of a plurality N of isomers is directed into a FAIMS device 220 (FIG. 2). The plurality of isomers may include at least three isomers and comprise isomers of a peptide or protein. In some embodiments, the ion beam is formed from a chromatographically separated sample.

In the next step 320, the CV at which the FAIMS device is operated is varied among a plurality M of values. In some embodiments, prior to analysis of the sample, CV tuning curves for each one of the N isomers are generated by introducing a calibration sample containing the corresponding pure isomer standards (i.e., in the absence of the other isomers) while scanning the CV across the operating range of the FAIMS device and recording the MS or MS/MS intensity at each CV. The tuning curves may be used to determine the CV values used for analysis, which will be described further below. It should be noted that if some of the isomers of interest are not available as pure calibrants, the tuning curves may be inferred by known deconvolution techniques.

Figure 4:
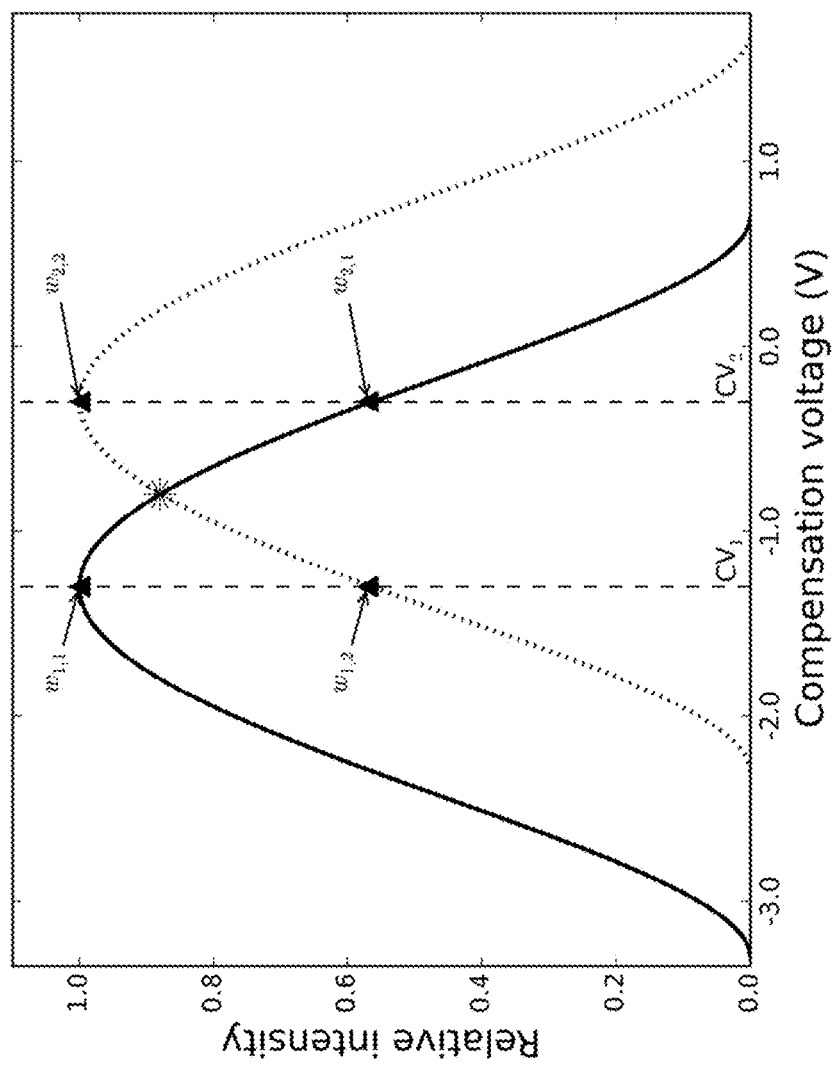
FIG. 4 is an example of a tuning curve for a sample ion beam containing two isomers, illustrating how compensation voltage values are selected for the SIM/SRM experiments.

In the next step 330, for each of the M CV values, an intensity of the ion beam transmitted by the FAIMS device—or product ions derived therefrom—is measured at a mass-to-charge ratio (m/z) corresponding to the plurality N of isomers. In some embodiments, the ion beam is mass filtered to only transmit ions of the m/z corresponding to the isomer and detect the transmitted ions by a technique known as single or selected-ion monitoring (SIM). SIM can be performed with one mass filter allowing selected ions to pass through and scanning for the isomers of a peptide or protein (analyte) of interest. The selected ions are passed through to a detector to measure signal intensity of the isomers at selected FAIMS CV values. In other embodiments, the transmitted ions are fragmented to generate product ions. These product ions are mass filtered and detected also at selected FAIMS CV values by a technique known as selected-reaction monitoring (SRM). By way of example, the ions of the m/z corresponding to the isomer are selected by a first quadrupole and pass through a second quadrupole where collision induced dissociation takes place. The isomers of interest collide at controlled kinetic energy with atoms or molecules of a collision gas, such as argon gas, resulting in their fragmentation and generation of characteristic product ions. These product ions continue to travel to a third quadrupole where they will be selected and mass selectively transmitted to the detector. It should be understood that regardless of the operation performed—SIM or SRM—intensity measurements are recorded at each of the M pre-determined FAIMS CV values at each scan. It is further noted that the inter-CV time, i.e., the wait time before initiation of intensity measurement following a change in the CV value, should be longer than the transit time of ions through the FAIMS device The set of FAIMS CV values used for measuring the intensities in step 330 may be selected using CV tuning curves previously acquired for each of the N isomers using pure isomer standards, e.g., a sample containing a single isomer in the absence of the other isomers. FIG. 4 is an example of tuning curves obtained for two isomers, with the tuning curve for the first isomer depicted as a solid line and the tuning curve for the second isomer depicted as a dotted line. The x-axis of the graph represents compensation voltages (CVs) scanned across the operating range of the FAIMS device. The y-axis of the tuning curve represents signal intensity (normalized to maximum transmission of that isomer) of the isomers. The tuning curves of FIG. 4 shows two selected CVs (at approximately −30 volts and −20 volts) and four weights ($w_{2,2}$, $w_{2,1}$, $w_{1,1}$, and $w_{1,2}$) marked at these compensation voltages. The weights constitute elements of a weighting matrix which will be explained in detail below, with each weight $w_{i,j}$ representing a weight at an $i^{th}$ value of the CV for the $j^{th}$ isomer. In this example, the CV values that are selected for analysis in step 330 correspond to the maxima of the tuning curves for each of the first and second isomers. It should be noted that more CVs and thus more weights can be chosen. For example, the crossing point where the two curves intersect (designated with an asterisk * symbol) or the outermost compensation voltages on the curve mirroring (i.e. equidistant from in opposite directions) this crossing point could have been selected.

Next, in step 340, the intensities of each of the plurality N of isomers at a non-separation (FAIMS off) condition is determined using the relation:

$$w\varnothing = \Phi \quad (1)$$

where w is an empirically derived weighting matrix, $\varnothing$ is a vector $\varnothing_1 \ldots \varnothing_N$ of the intensities of each of the plurality N of isomers at the non-separation condition, and $\Phi$ is a vector $\Phi_1 \ldots \Phi_M$ of the measured intensity values at each of the M values of the compensation voltage. As mentioned above, the elements of the weighting matrix w are determined using the CV tuning curves acquired using a set of calibration standards each containing one of the N isomers in pure form. $\Phi$, which is the aggregate flux or intensity of the isomers at each compensation voltage, is measured at the detector of the mass spectrometer using experiments such as SIM or SRM. Equation (1) may be solved for $\varnothing$ using any one of a number of regression techniques such as, but not limited to, matrix inversion, ordinary least squares, weighted least squares, or a generalized linear model (GLM) algorithm.

The following is one example of determining the intensity contribution of each of the plurality N of isomers using equation (1) in step 340. This example is explained using the M CV values and the selected matrix of weights (w) obtained from the tuning curve of FIG. 4. To simplify the example used herein, let M=2 CV values and N=2 isomers. It should be noted that the number of isomers can be less than the number of CV values. With these values, the relation $w\varnothing=\Phi$ can be written as follows:

$$\Phi_{cv1} = w_{1,1}\varnothing_{iso1} + w_{1,2}\varnothing_{iso2} \quad (2)$$

$$\Phi_{cv2} = w_{2,1}\varnothing_{iso1} + w_{2,2}\varnothing_{iso2} \quad (3)$$

where, for Equation (2), $\Phi_{cv1}$ is the ion flux at $CV_1$ measured at the detector, $w_{1,1}$ is the weight at $CV_1$ for isomer 1, $\varnothing_{iso1}$ is the flux of isomer 1 with the FAIMS device in the non-separating condition, $w_{1,2}$ is the weight at $CV_1$ acquired for isomer 2, and $\varnothing_{iso2}$ is the flux of isomer 2 with the FAIMS device in the non-separating condition, where, for Equation (3), $\Phi_{cv2}$ is the ion flux at $CV_2$ measured at the detector, $w_{2,1}$ is the weight at $CV_2$ for isomer 1, $\varnothing_{iso1}$ is the flux of isomer 1 with the FAIMS device in the non-separating condition, $w_{2,2}$ is the weight at $CV_2$ acquired for isomer 2, and $\varnothing_{iso2}$ is the flux of isomer 2 with the FAIMS device in the non-separating condition.

Equations (2) and (3) may be expressed as vectors in matrix, and each $\varnothing$ ($\varnothing_{iso1}$ and $\varnothing_{iso2}$) may be solved by matrix multiplication.

$$\begin{pmatrix} \Phi_{cv1} \\ \Phi_{cv2} \end{pmatrix} = \begin{pmatrix} w_{1,1} & w_{1,2} \\ w_{2,1} & w_{2,2} \end{pmatrix} \begin{pmatrix} \phi_{iso1} \\ \phi_{iso2} \end{pmatrix} \quad (4)$$

where $$\begin{pmatrix} \Phi_{cv1} \\ \Phi_{cv2} \end{pmatrix}$$

is the total ion flux at the selected CVs, $$\begin{pmatrix} w_{1,1} & w_{1,2} \\ w_{2,1} & w_{2,2} \end{pmatrix}$$

represents the combined weight matrix, and $$\begin{pmatrix} \phi_{iso1} \\ \phi_{iso2} \end{pmatrix}$$

represents the intensity contribution of each isomer.

$\emptyset_{iso1}$ and $\emptyset_{iso2}$ can be solved for by matrix inversion or other techniques—e.g., ordinary least squares, weighted least squares, or the GLM algorithm.

In some embodiments, the FAIMS device can be coupled to chromatographic equipment. Chromatographic equipment such as a liquid chromatograph (LC) may be used to elute or release ions from a sample into the mass spectrometer over a period of time. To be practically useful, a fast-switching FAIMS device with a short ion transit time should be used for LC-FAIMS-MS analysis. The CV switching time should be considerably faster than the inter-measurement time needed to correctly integrate an LC peak so that measurements can be taken at multiple CVs at each sample point. As one example, given an inter-measurement time for LC peak integration of 500 ms (or greater), the ion transit time of the FAIMS device should be in a range of about 10-50 milliseconds (ms) to scan or sweep several CVs at each point in the chromatographic peak.

Figure 5:
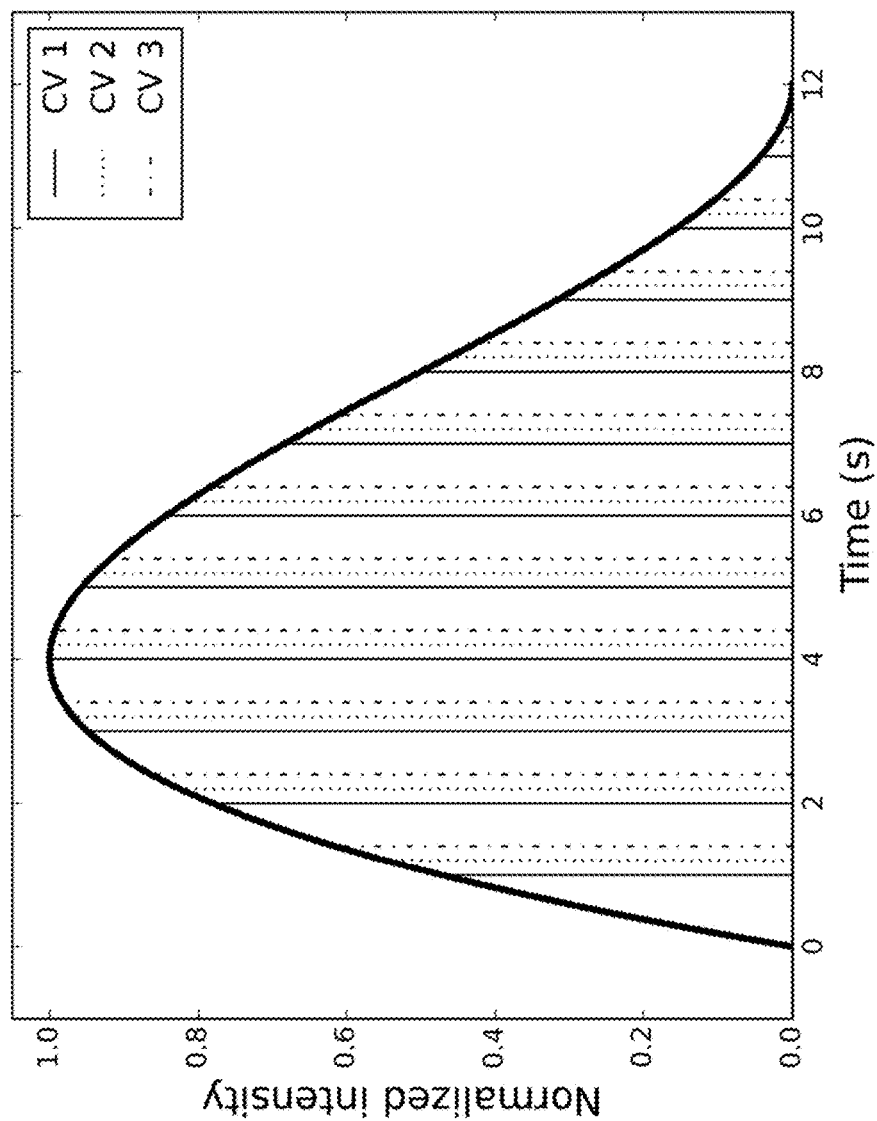
FIG. 5 is an example illustration of an LC chromatogram with multiple FAIMS CV scans carried out within each LC peak.

FIG. 5 is an example illustration of an LC chromatogram with multiple FAIMS CV scans carried out within each LC peak. FAIMS CV scans are completed within the duration of individual LC peaks by switching the CVs at each time point (e.g., $CV_1$ at time 1, $CV_2$ at time 2, $CV_3$ at time 3, etc.). FAIMS CV scans are completed within the duration of individual LC peaks by switching the CVs through the pre-determined lattice of settings at each point, such that the intensity measured at each CV at each point in time—approximately simultaneously. As mentioned above, the weights used for the matrix can be set using the CV tuning curves acquired for each of the isomers. From there, the intensity contribution of each isomer ($\emptyset_{iso1}, \emptyset_{iso2} \ldots \emptyset_{isoN}$) can be determined using equations (1)-(4) above and a regression technique, and the chromatographic peak can be integrated in the usual way.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A method of analyzing a sample by high-field asymmetric waveform ion mobility-mass spectrometry (FAIMS-MS), comprising:
   directing an ion beam containing ions of a plurality N of isomers into a FAIMS device;
   varying the compensation voltage (CV) at which the FAIMS device is operated among a plurality M of values;
   for each of the M CV values, measuring an intensity of the ion beam transmitted by the FAIMS device, or product ions derived therefrom, at a mass-to-charge ratio corresponding to the plurality N of isomers; and
   determining the intensities of each of the plurality N of isomers using the relation:

$w\emptyset = \Phi$ where w is an empirically derived weighting matrix, $\emptyset$ is a vector of the intensities of each of the plurality N of isomers with the FAIMS device in a non-separation condition, and $\Phi$ is a vector of the measured intensity values at each of M values of the compensation voltage.

2. The method of claim 1 where N is at least 3.

3. The method of claim 1 wherein the elements of the weighting matrix w are set using CV tuning curves acquired for each of the N isomers.

4. The method of claim 1 wherein the relation $w\emptyset = \Phi$ is solved for $\emptyset$ using one of: matrix inversion, ordinary least squares, weighted least squares and a generalized linear model (GLM) algorithm.

5. The method of claim 1 wherein the isomers comprise isomers of a peptide or protein.

6. The method of claim 1 wherein the step of measuring the intensity of the ion beam comprises mass filtering the ion beam to only transmit ions of the m/z corresponding to the isomer and detecting the transmitted ions.

7. The method of claim 1 wherein the step of measuring the intensity of the ion beam comprises mass filtering the ion beam to only transmit ions of the m/z corresponding to the isomer, fragmenting the transmitted ions to generate product ions, mass filtering the product ions to only transmit ions corresponding to the isomer, and detecting the transmitted product ions.

8. The method of claim 3 wherein the M CV values include at least one of the following determined from the tuning curves: CV values that maximize the transmission of each isomer, CV values at crossings of the tuning curves along a boundary of a region enclosed by all of the tuning curves, and outermost CV values on the tuning curves mirroring a nearest crossing point.

9. The method of claim 1 wherein the ion beam is formed from a chromatographically separated sample, and further comprising a step of integrating the determined intensity contribution of an isomer over a chromatographic peak.

10. The method of claim 1 wherein the step of determining the intensity contribution of each of the plurality N of isomers is performed in real time.

11. An apparatus, comprising:
    an ion source for generating a beam of ions from a sample;
    a high-field asymmetric waveform ion mobility (FAIMS) device positioned to receive the beam of ions from the ion source, the FAIMS device having a compensation voltage (CV) of variable magnitude applied thereto;
    at least one mass filter positioned to receive ions from the FAIMS device and operable to selectively transmit ions of a specified mass-to-charge ratio;
    a detector for generating a signal representative of a measured intensity of ions transmitted by the at least one mass filter; and
    a data/control system programmed to perform steps of:
    varying the CV at which the FAIMS device is operated among a plurality M of values;
    causing the at least one mass filter to transmit ions at an m/z corresponding to a plurality N of isomers contained in the sample; and determining the intensities of each of the plurality N of isomers using the relation:

$$w\emptyset = \Phi$$

where w is an empirically derived weighting matrix, $\emptyset$ is a vector of the intensities of each of the plurality N of isomers with the FAIMS device in a non-separation condition, and $\Phi$ is a vector of the measured intensity values at each of M of the compensation voltage.

12. The apparatus of claim 11 where N is at least 3.

13. The apparatus of claim 11 wherein the elements of the weighting matrix w are set using CV tuning curves acquired for each of the N isomers.

14. The apparatus of claim 11 wherein the relation $w\emptyset = \Phi$ is solved for $\emptyset$ using one of: matrix inversion, ordinary least squares, weighted least squares and a generalized linear model (GLM) algorithm.

15. The apparatus of claim 11 wherein the isomers comprise isomers of a peptide or protein.

16. The apparatus of claim 13 wherein the M CV values include at least one of the following determined from the tuning curves: CV values that maximize the transmission of each isomer, CV values at crossings of the tuning curves along a boundary of a region enclosed by all of the tuning curves, and outermost CV values on the tuning curves mirroring a nearest crossing point.

17. The apparatus of claim 11 wherein the ion beam is formed from a chromatographically separated sample, and further comprising a step of integrating the determined intensity contribution of an isomer over a chromatographic peak.

18. The apparatus of claim 11 wherein the step of determining the intensity contribution of each of the plurality N of isomers is performed in real time.

* * * * *